United States Patent [19]

Lesenko

[11] Patent Number: 5,635,443
[45] Date of Patent: Jun. 3, 1997

[54] COMPOSITION TO ENHANCE CUT FLOWERS

[75] Inventor: Kenneth W. Lesenko, Clifton, N.J.

[73] Assignee: Florasynth, Inc., Teterboro, N.J.

[21] Appl. No.: 476,686

[22] Filed: Jun. 7, 1995

[51] Int. Cl.$^6$ ............................................. A01N 3/02
[52] U.S. Cl. ................................... 504/114; 504/115
[58] Field of Search ............................... 504/114, 115

[56] References Cited

U.S. PATENT DOCUMENTS

| | | | |
|---|---|---|---|
| 4,256,773 | 3/1981 | Itoga et al. | 426/415 |
| 5,102,715 | 4/1992 | Zetterquist | 428/137 |
| 5,171,351 | 12/1992 | Yamamoto et al. | 504/115 |
| 5,213,604 | 5/1993 | Saito et al. | 504/114 |
| 5,228,899 | 7/1993 | Itoh et al. | 504/115 |
| 5,252,537 | 10/1993 | De Winter-Scailteur | 504/114 |
| 5,366,954 | 11/1994 | Bestwick et al. | 504/114 |

*Primary Examiner*—Richard L. Raymond
*Assistant Examiner*—Brian G. Bembenick
*Attorney, Agent, or Firm*—Scully, Scott, Murphy & Presser

[57] ABSTRACT

The present invention relates to a composition for maintaining the freshness and enhancing the fragrance of cut flowers. More specifically, the present invention relates to liquid compositions into which the stems of cut flowers can be immersed, thereby providing a medium for maintaining the freshness and enhancing the fragrance of the cut flowers, comprising at least one or more surfactant, at least one fragrance, at least one fragrance solvent, water, acetylsalicylic acid or acetylsalicylsalicylic acid, sodium chloride, sodium bicarbonate and at least one antifoaming agent.

12 Claims, No Drawings

COMPOSITION TO ENHANCE CUT FLOWERS

FIELD OF THE INVENTION

The present invention relates to a composition for maintaining the freshness and enhancing the fragrance of cut flowers. More specifically, the present invention relates to liquid compositions into which the stems of cut flowers can be immersed, thereby providing a medium for maintaining the freshness and enhancing the fragrance of the cut flowers.

BACKGROUND OF THE INVENTION

A plant receives essential nutrients and water to sustain life from the soil. Nutrients and water are absorbed through the roots of the plant and travel to the leaves and flowers through a network of ducts. When flowers and leaves are removed from the plant, the nutrient reserve in the leaves and flowers of the plant part rapidly becomes exhausted, whereupon the flowers wilt. To prolong the life of cut flowers, the water and nutrients normally supplied to the leaves and flowers by the roots must be provided. Traditionally, to prolong the life of fresh cut flowers, the stem of the flower is placed in water. Although water prolongs the freshness of cut flowers, it does not contain the essential nutrients required to prolong the life of the flower.

The present invention provides a novel composition for maintaining the freshness and enhancing the fragrance of cut flowers which alleviates many of the limitations associated with conventional methods of maintaining cut flowers.

SUMMARY OF THE INVENTION

It is the object of the present invention to provide a means for maintaining the freshness of cut flowers using the composition described herein.

Accordingly, the present invention relates to a novel composition for maintaining the freshness and enhancing the fragrance of cut flowers comprising at least one surfactant, at least one fragrance, at least one fragrance solvent, water, acetylsalicylic acid or acetylsalicylsalicylic acid, sodium chloride, sodium bicarbonate and at least one antifoaming agent. The composition has a pH ranging from 7.0 to 8.0. Preferably, it further comprises a plant hormone and plant food.

The present invention further relates to a method for maintaining the freshness and enhancing the fragrance of cut flowers comprising immersing the stems of the flowers in water containing a composition comprising at least one surfactant, at least one fragrance, at least one fragrance solvent, water, acetyl salicylic acid or acetylsalicylsalicylic acid, sodium chloride, sodium bicarbonate, and at least one antifoaming agent. The composition has a pH ranging from 7.0 to 8.0. Preferably, it further comprises a plant hormone and plant food.

DETAILED DESCRIPTION OF THE INVENTION

There has been discovered in accordance with the present invention a novel composition for maintaining the freshness and enhancing the fragrance of cut flowers. Specifically, the present invention is directed to a composition comprising at least one surfactant, at least one fragrance, at least one fragrance solvent, water, acetylsalicylic acid or acetylsalicylsalicylic acid, sodium chloride, sodium bicarbonate, and at least one antifoaming agent.

The surfactants used in accordance with the present invention are preferably nonionic, however, amphoteric and anionic surfactants can also be used in the composition solution described herein. Examples of nonionic surfactants include, for example, alcohol ethoxylates, alkylphenol ethoxylates, carboxylic acid esters, glycerol esters, polyoxyethylene esters, anhydrosorbitol esters, ethoxylated anhydrosorbital esters, glycol esters of fatty acids, polyoxyethylene fatty acid amides, amide esters, amine oxides, and polyoxyethylene-co-oxypropylenes. Examples of amphoteric surfactants include, for example, imidazoline derivatives, imidazolinium derivatives and betaine derivatives. Anionic surfactants used in the composition described by the present invention include, for example, alkyl sulfates, alkylbenzenesulfonates, alkylarenesulfonates, naphthalenesulfonates, petroleum sulfonates, alcohol sulfates, phosphate esters, N-cylsarcosinates, alkyl monoglyceride sulfates, N-acyl methyltaurates, alpha-olefinsulfonates, polyalkoxycarboxylates and alkyl sulfoacetates.

Numerous commercially available surfactants can be used in accordance with the present invention including, for example, polyoxyethylene sorbitan monolaurate, polyoxyethylene sorbitan monopalmitate, polyoxyethylene sorbitan monostearate, ethoxylated alkyl phenols, and hydrogenated castor oils, any of the foregoing polyoxyethylene or ethoxylated compounds containing 2 to 40 ethoxy units.

In a preferred embodiment, the surfactant is selected from the group consisting of polyoxyethylene sorbitan esters, ethoxylated alkyl phenols, and hydrogenated castor oils.

In the most preferred embodiment, the surfactant is polyoxyethylene (20) sorbitan monolaurate.

The composition described in accordance with the present invention contains at least one surfactant in an amount sufficient to solubilize the fragrance components in water. In a preferred embodiment, the composition contains at least one surfactant in an amount ranging from 25% to 45% by weight of the composition. In a more preferred embodiment, the composition contains about 30% to 40% by weight of at least one surfactant and most preferably about 34% to about 38% of surfactant.

The fragrances used in accordance with the present invention are soluble in oil or water. In a preferred embodiment, the fragrance is oil-soluble. As used herein, a fragrance is a substance that has a sweet or pleasant odor. Fragrances that can be used in the composition of the present invention include those imparting a floral or herbal aroma. Specific fragrances can be determined from industry known handbooks and from fragrance suppliers wherein fragrances are classified by such characteristics.

The composition described in accordance with the present invention contains at least one fragrance in an amount sufficient to enhance to the fragrance of the cut flowers. In a preferred embodiment, the composition contains at least one fragrance in an amount ranging from 8% to 16% by weight of the composition. In a more preferred embodiment, the composition contains about 10% to 15% of at least one fragrance and yet more preferably about 11% to about 14% of fragrance.

The composition described herein contains a fragrance solvent component in an amount sufficient to solubilize the fragrance into water. This component can comprise one compound or more than one compound. In a preferred embodiment, the composition contains the fragrance solvent component in an amount ranging from 12% to 20% by weight of the composition. In a more preferred embodiment, the fragrance solvent component comprises approximately 15% to 20% by weight of the composition.

The compound or compounds used as the fragrance solvent component in the present invention depend on the identity of the compound or compounds of which the fragrance itself is comprised. However, suitable fragrance solvent components and amounts can readily be ascertained without undue experimentation. Compounds which are generally useful as fragrance solvents include, for example, ethanol, glycerine and lower glycols such as propylene and dipropylene.

In a preferred embodiment, the composition contains as fragrance solvents, both ethanol and glycerine.

Also contained in the composition described herein is one or both of acetylsalicylic acid or acetylsalicylsalicylic acid in an amount sufficient to enhance water uptake by the cut flowers. In a preferred embodiment, the composition contains acetylsalicylic acid or acetylsalicylsalicylic acid in an amount ranging from 0.005% to 0.015% by weight of the composition. In a more preferred embodiment, the composition contains acetylsalicylic acid or acetylsalicylsalicylic acid in an amount approximately 0.01% by weight of said composition.

The composition of the present invention further contains sodium chloride and sodium bicarbonate. Sodium chloride is present in the composition in an amount sufficient to maintain the osmotic pressure of the composition. In a preferred embodiment, the composition contains 0.5% to 2.0% sodium chloride by weight of the composition. In a more preferred embodiment, the composition contains approximately 1.2% sodium chloride by weight of the composition. Sodium bicarbonate is present in the composition in an amount sufficient to maintain the pH of the composition to a desired value between 7.0 and 8.0. In a preferred embodiment, the composition contains sodium bicarbonate in an amount ranging from 0.03% to 1.3% of the composition. In a more preferred embodiment, the composition contains sodium bicarbonate in an amount to adjust the pH to a level in that range, which amount is typically approximately 0.8% by weight of the composition.

The composition described in accordance with the present invention further comprises at least one antifoaming agent in an amount sufficient to retard or reduce the formation of foam by the composition. An antifoaming agent for purposes of the present invention is a chemical that reduces the tendency of the composition to generate foam upon shaking or agitation. Examples of antifoaming agents include, for example, silicones, alcohols and lipids. Commercially available antifoaming agents which can be used in accordance with the present invention include, for example, biphenylhexamethicone, dimethicone, dimethiconol, hexamethyldisiloxane, petroleum distillate, phenyl trimethicone, silica silylate, simethicone, tetraethyl decynediol and trimethylsilocysilcate. In a preferred embodiment, the antifoaming agent is polydimethylsiloxane, silica, stearate or alginate emulsifiers, sorbic acid or benzoic acid.

In a preferred embodiment the composition described by the present invention further contains a plant hormone and plant food in an amount ranging from between 0.0005% to 0.0015% of said composition. In a more preferred embodiment, the plant hormone and plant food are each present in an amount approximately 0.001% by weight of the composition. A plant hormone is defined herein as an organic substance other then a nutrient that, in minute amounts, modifies a plant physiological process. Plant hormones that can be used in the composition described herein include for example, indole 3-acetic acid, gibberellin and auxins.

In a preferred embodiment, the plant hormone is indole 3-acetic acid.

As used herein, plant food is an inorganic or organic nutrient absorbed by plants from a liquid medium in which the plant is placed. Plant foods used in accordance with the present invention include, for example, D,L glyceraldehyde, sucrose, gibberellin, kinetins, zeatin and 6-benzylamino purine.

In a preferred embodiment, the plant food is D,L glyceraldehyde.

The balance of the composition, typically 25–50 wt. %, is water. Preferably, the water is deionized.

The composition described in accordance with the present invention can be produced using a number of conventional techniques. For example, the composition described herein may be prepared by mixing two compositions, compositions A and B separately, and then adding composition A to composition B. Composition A may be prepared by mixing the surfactant and fragrance components with the fragrance solvent and plant hormone until a uniform solution is obtained. The quantities of each ingredient may be increased or decreased depending upon the amount of the composition desired. Composition B may be prepared by mixing water, acetylsalicylsalicylic acid and/or acetylsalicylic acid, and plant food together and subsequently adding more fragrance solvent, sodium chloride, sodium bicarbonate and antifoaming agent.

The present invention is further directed to a method for maintaining the freshness and enhancing the fragrance of floral parts comprising immersing the stem of the flower in the composition described herein. To further enhance the freshness of the cut flowers, using the method of the present invention, the stem of the fresh cut flowers should be immersed in the composition solution described herein immediately after being cut.

In order to further illustrate the present invention, the following example is presented. It should be understood that the invention is not limited to the specific example or the details described therein.

EXAMPLE 1

A composition described in accordance with the present invention was produced by adding composition A to composition B and mixing until a uniform solution was produced. The amounts of each component provided below are in percent by weight of the final product solution. Composition A contained the following components: (a) a surfactant, TWEEN 20 (polyoxyethylene (20) sorbitan monolaurate), in an amount approximately 36% by weight of the solution, (b) a fragrance, in an amount approximately 12% by weight of the solution, (c) a fragrance solvent, ethanol, in an amount approximately 6% by weight of the solution and (d) a plant hormone, indole 3-acetic acid, in an amount approximately 0.001% by weight of the solution. These components were mixed for a few minutes until a uniform solution was obtained.

Composition B was prepared in two phases. In phase 1, the following components were premixed: (a) deionized water, in an amount approximately 34.0% by weight of the solution, (b) acetylsalicylsalicylic acid, in an amount approximately 0.01% by weight of the solution, and (c) plant food, in an amount approximately 0.001% by weight of the solution. In phase 2, the following components were added to the solution of phase 1: (a) a fragrance solvent, glycerine, in an amount approximately 10% by weight of the solution, (b) sodium chloride, in an amount approximately 1.2% by weight of the solution, (c) sodium bicarbonate, in an amount approximately 0.8% by weight of the solution, and (d) an antifoaming agent, in an amount approximately 0.02% by weight of the solution.

Compositions within the scope of the present invention include aqueous concentrates which can be diluted with water to create solutions useful for preserving and enhancing cut flowers. Also, compositions within the scope of the present invention include the solutions as diluted and ready to use. The amounts of the components other than water retain the same relative proportions to each other in the concentrates and the fully diluted solutions as shown in the table below. Typical dilution ratios can range from 1:1 (wt.) to 10:1 or 20:1. In use, fresh cut flowers are immersed in the solution comprising the diluted composition described herein to maintain the freshness and enhance the fragrance of the fresh cut flowers.

| Component | Amount (wt. %) in Concentrate | Amount Fully Diluted (wt. %) |
|---|---|---|
| Surfactant | 35–65 | 25–45 |
| Fragrance | 10–30 | 8–16 |
| Fragrance solvent | 15–35 | 12–20 |
| Acetylsalicylic/ acetylsalicyl- salicylic acid(s) | 0.005–0.03 | 0.005–0.015 |
| Sodium Chloride | 0.6–4 | 0.5–2.0 |
| Sodium Bicarbonate | 0.03–2.6 | 0.03–1.3 |
| Antifoam | 0.01–0.06 | 0.01–0.03 |
| Plant Hormone | 0.005–0.003 | 0.0005–0.0015 |
| Plant Food | 0.005–0.003 | 0.0005–0.0015 |
| Water | 2.5–5.0 | 25–50 |

I claim:

1. A composition for maintaining the freshness and enhancing the fragrance of cut flowers comprising: (a) at least one surfactant in an amount from 25% to 45% by weight of said composition, (b) at least one fragrance in an amount from 8% to 16% by weight of said composition, (c) at least one fragrance solvent in an amount from 12% to 20% by weight of said composition, (d) water in an amount from 25% to 45% by weight of said composition, (e) one or both of acetylsalicylic acid and acetylsalicylsalicylic acid in an amount from 0.005% to 0.015% by weight of said composition, (f) sodium chloride in an amount from 0.5% to 2.0% by weight of said composition, (g) sodium bicarbonate in an amount from 0.03% to 1.3% of said composition, and (h) at least one antifoaming agent in an amount from 0.01% to 0.03% of said composition.

2. The composition of claim 1 wherein said composition further comprises (i) a plant hormone in an amount from 0.0005% to 0.0015% of said composition and (j) plant food in an amount from between 0.0005% to 0.0015% of said composition.

3. The composition according to claim 1 wherein said surfactant is selected from the group consisting of polyoxyethylene sorbitan monolaurate, monopalmitate monostearate, ethoxylated alkyl phenols and hydrogenated castor oils.

4. The composition according to claim 1 wherein said fragrance solvent is one or more compounds selected from the group consisting of ethanol, glycerine, propylene and dipropylene.

5. The composition according to claim 2 wherein said plant hormone is selected from the group consisting of indole 3-acetic acid, gibberellin and auxins.

6. The composition according to claim 2 wherein said plant food is selected from the group consisting of D,L-glyceraldehyde, sucrose, gibberellin, kinetins, zeatin and 6-benzylamino purine.

7. A method for maintaining the freshness and enhancing the fragrance of a cut flower comprising immersing the stem of said cut flower in a composition comprising (a) at least one surfactant in an amount from 25% to 45% by weight of said composition, (b) at least one fragrance in an amount from 8% to 16% by weight of said composition, (c) at least one fragrance solvent in an amount from 12% to 20% by weight of said composition, (d) water in an amount from 25% to 45% by weight of said composition, (e) one or both of acetylsalicylic acid and acetylsalicylsalicylic acid in an amount from 0.005% to 0.015% by weight of said composition, (f) sodium chloride in an amount from 0.5% to 2.0% by weight of said composition, (g) sodium bicarbonate in an amount from 0.03% to 1.3% of said composition, and (h) at least one antifoaming agent in an amount from 0.01% to 0.03% of said composition.

8. The method of claim 7 wherein said composition further comprises (i) a plant hormone in an amount from 0.0005% to 0.0015% of said composition and (j) plant food in an amount from 0.0005% to 0.0015% of said composition.

9. The method according to claim 7 wherein said surfactant is selected from the group consisting of polyoxyethylene sorbitan monolaurate, polyoxyethylene sorbitan monopalmitate, polyoxyethylene sorbitan monostearate, ethoxylated alkyl phenols and hydrogenated castor oils.

10. The method according to claim 7 wherein said fragrance solvent is one or more compounds selected from the group consisting of ethanol, glycerine, propylene and dipropylene.

11. The method according to claim 8 wherein said plant hormone is selected from the group consisting of indole 3-acetic acid, gibberellin and auxins.

12. The method according to claim 8 wherein said plant food is selected from the group consisting of D,L-glyceraldehyde, sucrose, gibberellin, kinetins, zeatin and 6-benzylamino purine.

* * * * *